United States Patent
Peleg et al.

(10) Patent No.: US 6,406,690 B1
(45) Date of Patent: Jun. 18, 2002

(54) *BACILLUS FIRMUS* CNCM I-1582 OR *BACILLUS CEREUS* CNCM I-1562 FOR CONTROLLING NEMATODES

(75) Inventors: Itzhak Peleg, Maccabim; Katherina Feldman, Jerusalem, both of (IL)

(73) Assignee: Minrav Industries Ltd., Jerusalem (IL)

( * ) Notice: Subject to any disclaimer, the term of this patent is extended or adjusted under 35 U.S.C. 154(b) by 0 days.

(21) Appl. No.: 08/945,047

(22) PCT Filed: Apr. 16, 1996

(86) PCT No.: PCT/US96/05270

§ 371 (c)(1),
(2), (4) Date: Jul. 10, 1998

(87) PCT Pub. No.: WO96/32840

PCT Pub. Date: Oct. 24, 1996

(30) Foreign Application Priority Data

Apr. 17, 1995 (IL) .................................................. 113394

(51) Int. Cl.[7] .......................... A01N 25/00; A01N 63/00; C12N 1/00; C12N 1/20
(52) U.S. Cl. ................. 424/93.46; 424/405; 435/252.5; 435/832; 435/834
(58) Field of Search ................................ 424/405, 93.1, 424/93.46; 435/252.1, 822, 262.5, 252.5, 834, 832

(56) References Cited

U.S. PATENT DOCUMENTS

| | | | | |
|---|---|---|---|---|
| 5,072,558 A | * | 12/1991 | Obata et al. ................. | 514/259 |
| 5,378,460 A | * | 1/1995 | Zuckerman et al. ... | 424/93.461 |
| 5,888,801 A | * | 3/1999 | Warren et al. ........... | 435/252.5 |
| 5,976,564 A | * | 11/1999 | Liu et al. ..................... | 424/405 |

* cited by examiner

*Primary Examiner*—David M. Naff
*Assistant Examiner*—Deborah K. Ware
(74) *Attorney, Agent, or Firm*—Mark M. Friedman

(57) ABSTRACT

A biologically pure strain of *Bacillus firmus* (CNCM I-1582) possessing nematicidal activity is provided. Also provided are compositions containing and methods for employing the *Bacillus firmus* strain and a biologically pure strain of *Bacillus cereus* (CNCM I-1562) possessing nematicidal activity. Nematicidally active mutants of these strains are also provided. Further disclosed are nematicidal compositions for use in plant protection based upon these bacterial strains or mutants thereof. Further disclosed are methods for controlling plant-pathogenetic nematodes which include use of these bacterial strains or mutants thereof. The strains find utility in controlling root-knot disease causing nematodes, for example those belonging to the species Meloidogyne.

14 Claims, 2 Drawing Sheets

BACILLUS FIRMUS CNCM I-1582 OR BACILLUS CEREUS CNCM I-1562 FOR CONTROLLING NEMATODES

FIELD OF THE INVENTION

This application claims priority from PCT/US96/05270 filed Apr. 16, 1996 and from Israel patent application IL 113394 filed Apr. 17, 1995.

The present invention relates to nematicidal bacterial strains, and particularly to strains which affect plant-pathogenic nematodes. The invention also relates to agricultural nematicidal compositions as well as to methods of controlling plant pathogenic nematodes.

BACKGROUND OF THE INVENTION

Root-knot is one of the most serious plant diseases in the world. Throughout the world, root-knot disease causes an average annual yield loss of about 5%. The greatest losses however, occur to those who can least afford it, namely, the farmers of underdeveloped countries. Their losses may be as much as 25–50% over a wide area of available farmland. In addition, there are several indirect losses associated with root-knot disease including secondary attack by other pathogens (in combination with other pathogens, root-knot disease can be disastrous); inefficient utilization of fertilizer and water; and high cost of chemical treatment.

The most common parasites causing this disease belong to the Meloidogyne spp. These nematodes have been shown to parasitize more than 3000 plant species including all the main crop families. Root-knot nematodes are found in all climate zones and in most types of soil. They are more active in finding and attacking plants in warm climates than in colder regions. Plants infected by root-knot nematodes display one or both of the following symptoms: root systems are galled, shortened or reduced by rotting; the stems are shortened and thickened, and the leaves do not grow normally.

The most distinctive symptom caused by root-knot nematodes are the galls or knots on the roots. The galls vary in size from a pin head to compound galls of more than 2.5 cm in diameter. They are irregular, spherical or spindle shaped and most often found on tender rootlets. These structures host one to several hundred female nematodes, which remain stationary throughout their life cycle and feed inside the root.

In light of their global economic impact on commercial crops, there is an urgent need to find an efficient way of controlling root-knot nematodes. Until now, chemicals such as methyl bromide or ethyl dibromide have been used to control nematodes. However, development of resistance by the pathogens to nematicidal chemicals, as well as a heightened awareness of short and long term ecological damage caused by these and other chemicals, have increased interest in developing a bio-nematicidal product which acts specifically against its target nematode without causing ecological damage.

SUMMARY OF THE INVENTION

It is an object of the present invention to provide bacterial strains having nematicidal activity against root-knot causing nematodes.

It is a further object of the present invention to provide an agricultural composition useful for protecting plants against root-knot nematodes.

It is an additional object of the present invention to provide a method of controlling plant-pathogenic nematodes.

In accordance with the present invention, new bacterial strains of the species *B. firmus* have been found which possess a nematicidal activity. These two bacterial strains are termed herein as *Bacillus firmus* strain CNCM I-1582 and *Bacillus cereus* strain CNCM I-1562. Both strains have been deposited with the Collection Nationale de Cultures de Microorganismes (CNCM), Institute Pasteur, France, at the following date and under the following Accession Nos.:

| Strains | Deposit date | Accession No. |
| --- | --- | --- |
| *Bacilius firmus* strain | May 29, 1995 | CNCMI-1582 |
| *Bacillus cereus* strain | April 13, 1995 | CNCMI-1562 |

Use of the *Bacillus firmus* strain CNCM I-1582 and *Bacillus cereus* strain CNCM I-1562 strains is currently a preferred embodiment of the invention. Other strains useful in accordance with the present invention are various mutant strains derived from the *Bacillus firmus* strain CNCM I-1582 and *Bacillus cereus* strain CNCM I-1562 strains which possess nematicidal activity. Mutant strains are at times obtained spontaneously but can also be obtained by mutagenesis, e.g. by the use of irradiation or mutagens. As will be appreciated by the artisan, it is possible to induce various kinds of mutations which will not cause a substantial change in the bacteria's nematicidal activity and their ability to exert this nematicidal activity when administered to soil in which the crops to be protected grow.

The present invention thus provides, by one of its aspects, a strain of bacteria belonging to the species *B. firmus* and possessing nematicidal activity, such strain being a member of the group consisting of EIP-N1 (CNCM I-1556), EIP-N2 (CNCM I-1562), and nematicidally active mutants of said *Bacillus firmus* strain CNCM I-1582 or *Bacillus cereus* strain CNCM I-1562.

Also provided by the present invention are pure cultures of bacteria, selected from the group consisting *Bacillus firmus* strain CNCM I-1582 or a *Bacillus cereus* strain CNCM I-1562 nematicidally active mutant of said *Bacillus firmus* strain CNCM I-1582 or *Bacillus cereus* strain CNCM I-1562.

According to another aspect of the present invention there is provided a nematicidal composition for use in plant protection comprising as active ingredient an effective amount of a nematicidal bacteria or of spores thereof, the bacteria being of a strain selected from the group consisting of *Bacillus firmus* strain CNCM I-1582 *Bacillus cereus* strain CNCM I-1562 and a nematicidally active mutant of said *Bacillus firmus* strain CNCM I-1582 or *Bacillus cereus* strain CNCM I-1562 together with a carrier compatible with the nematicidal bacteria.

In accordance with the preferred embodiment of the invention, the composition is supplemented by one or more supplements which improve or intensify the ability of the bacteria to exert their nematicidal activity. Supplements, may for example be nutrients such as gelatin, gelatin hydrolysate, cotton seed meal and casein hydrolysate.

According to another aspect of the present invention, there is provided a method for controlling plant-pathogenic nematodes, comprising applying to the plant roots or to the soil environment in which the plant grow, an effective amount of bacteria or spores thereof, the bacteria being of a strain selected from the group consisting of *Bacillus firmus* strain CNCM I-1582 *Bacillus cereus* strain CNCM I-1562 and a nematicidally active mutant of *Bacillus firmus* strain CNCM I-1582 or *Bacillus cereus* strain CNCM I-1562. The bacteria may be introduced into the soil by applying the bacteria under the soil within a liquid carrier. Alternatively, the bacteria may also be in a dry formulation and admixed with the soil, e.g. prior to planting or seeding. The bacteria may also be applied by impregnating plant roots or seeds prior to planting or seeding thereof into the soil, with a liquid formulation comprising the bacteria.

Another aspect of the present invention is a pot mix comprising bacteria of the invention.

The bacterial strains of the present invention are useful in controlling nematodes causing root-knot disease, and particularly those which belong to the Meloidogyne spp. However, the bacteria of the invention may also be effective against other pathogenic nematodes such as cyst nematodes.

Figure 1:
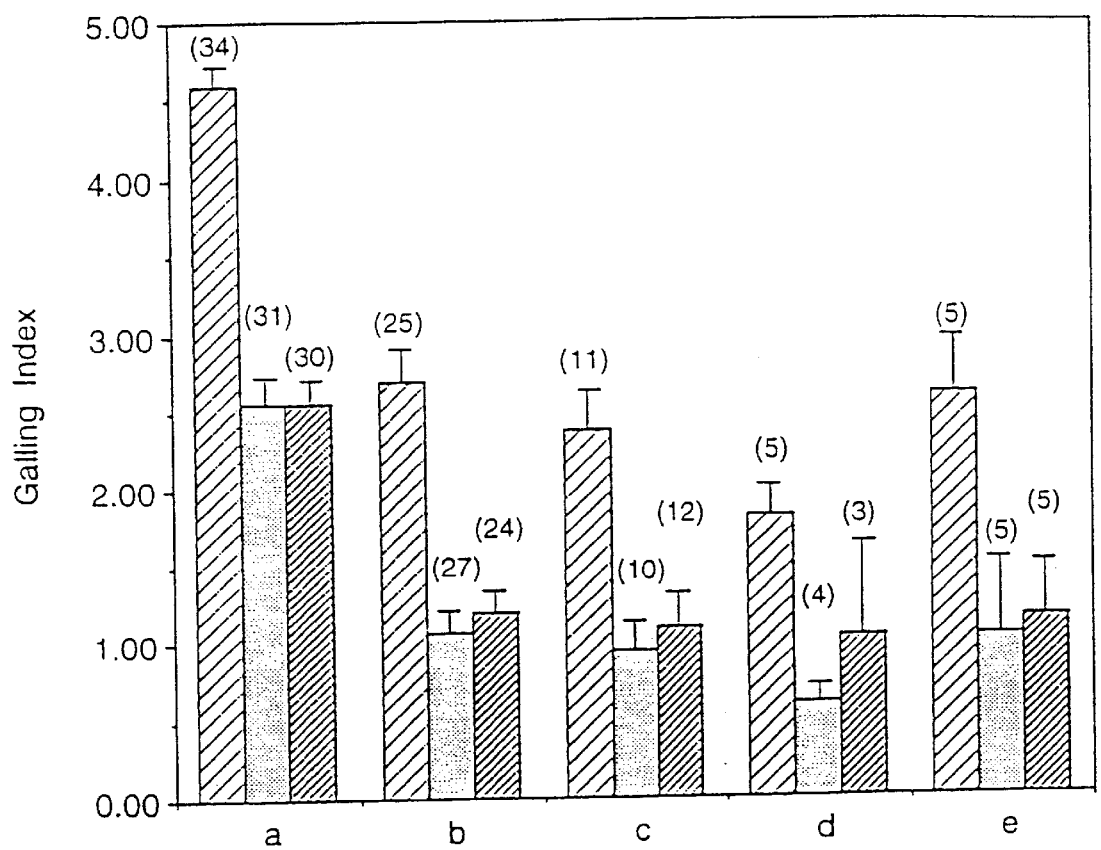
FIG. 1 shows results of experiments in which the activity of *Bacillus firmus* strain CNCM I-1582 (■), *Bacillus firmus* strain CNCM I-1562 (▨) in controlling nematodes, as compared to control (☐), was determined under greenhouse conditions.

The present invention will be better understood from the following detailed description of preferred embodiments, taken in conjunction with the following figures, which summarizes the results of a number of experiments in which the strains of the invention were used to control the pathogenic activity of nematodes in the greenhouse or in microplots.

DETAILED DESCRIPTION OF PREFERRED EMBODIMENTS

Materials and Methods

I. Identification

The strains were sent to the Deutsche Sammlung von Mikro-organismen und Zellkuturen GmbH (DSM) for identification, using partial 16S rDNA sequence hybridization.

II. Growth Conditions

The strains grow on MBS liquid medium (medium for bacillus sporulation) containing:

GE 90F (commercial hydrolysate of gelatin)—10 gr/L *Bacillus firmus* strain CNCM I-1582 or tryptose—5 gr/L *Bacillus cereus* strain CNCM I-1562;

Yeast extract—2 gr/L;

$KH_2PO_4$—6.8 gr/L;

and the following trace elements:

$MgSO_4 \cdot 7H_2O$—0.3 gr/L;

$MnSO_4$—0.02 gr/L;

$FeSO_3$—0.02 gr/L;

$ZnSO_4 \cdot 7H_2O$—0.02 gr/L;

$CaCl_2$—0.2 gr/L;

pH: 7.4 (adjusted with NaOH).

EIP-N2 can also grow on Nutrient agar medium (Difco).

The strains were grown in either 2-liter Erlenmeyer flasks or in 100–500 liter fermentors in a batch fermentation for 48–72 hours at a temperature of 30° C. The Erlenmeyer was agitated at a speed of 180 RPM.

III. Counting

The medium was centrifuged (5000*g, 20 min, RT) and the pellet containing a mixture of spores and vegetative cells was dissolved in a small amount of distilled water. Samples were seeded before and after heating at 70° C. for 10 min for counting the total cell number and the number of spores, respectively.

The total spore number is usually 75–90% of the total cell count. A typical yield is $5 \cdot 10^8$ spores/ml.

IV. Stability

The spores showed 100% viability after 6 months in a dry form at room temperature. The spores can also be stored under the following conditions:

1) As a paste at −70° C. for at least six months;
2) By freeze-drying of spores in 10% skim milk solution and storage at 4° C.;
3) In slants stored at 4° C.;
4) The spores can be dried in an oven in the presence of peat moss or silica.

Under the last three conditions, the viability is for at least one year.

V. Proteolytic Activity

Proteolytic activity was determined by measuring the increase in optical density as a result of the release of a colored product into solution following the breakdown of Azocasein (Sigma).

The reaction mixture (1 ml) contained 6 mg Azocasein in 0.5 ml and 0.5 ml from the supernatant of the growth medium, 0.05 M Tris HCl buffer PH 7.6 containing 5 mM $CaCl_2$. The reaction mixture was incubated for 15 min at 37° C., and the reaction was terminated by the addition of 0.5 ml of 10% TCA. Following an additional incubation of 30 min on ice and centrifugation (10,000 RPM, 15 min), the increase in optical density at a wavelength of 400 nm was determined vs. a control (1 ml of reaction mixture without growth medium supernatant).

VI. Collagenolytic activity

Collagenolytic activity was assayed by following the cleavage of a synthetic peptide (4-Phenylazobenzyloxycarbonil-Pro-Leu-Gly-D-Arg) by collagenase, and determining the amount of colored product released into the solution.

The reaction mixture included 0.5 ml supernatant of the growth medium, 2 ml of the synthetic peptide (stock solution contained 10 mg peptide in 0.1 ml methanol and 10 ml veronal buffer PH 7.6), and 0.25 ml of 50 mM N-Ethylmaleimide.

The mixture was incubated at 37° C. for 20 min and the reaction was terminated by the addition of 1 ml of 0.5% citric acid and 5 ml of ethyl acetate mixture to 0.5 ml of the reaction mixture. Following agitation for 20 sec, the solution was separated into two phases of which the upper phase was separated and its absorbance determined at a wave length of 320 nm. 1 O.D./$6 \cdot 10^7$ cells equals 1 enzyme unit.

VII. Application Techniques

1. Mixing spores with soil in the presence or absence of supplements ($5 \cdot 10^7$ spores/gr soil): in pot experiments, 500 gr of soil were used, while in microplot tests, buckets containing 15–30 kg soil were used. The chemical agent used as a control in the microplot tests is Nemacur® (Bayer).

2. Addition of spores formulated in peat moss or silica to pot soil or to seedling growth chambers: spores were mixed with either peat moss or silica and dried out in an oven (40° C., overnight) prior to application.

VIII. Nematicidal Activity Assay

In all the experiments, tomato seedlings (Na'ama strain) were used. Soil was artificially infested with 0.7 nematodes/gr soil, and the seedlings were planted in the infested soil. Larvae were prepared from egg masses developed on tomato roots. Each trial continued for 30 days.

The quantitation is based on percent change in a "Galling Index" scale ranging between 0–5, whereas "0" represents no galls on the roots and "5" represents maximum root infestation.

Results

I. *Bacillus firmus* strain CNCM I-1582

The *Bacillus cereus* strain CNCM I-1562 strain was isolated from soil obtained from the central plain area of Israel, following greenhouse pot experiments during which the soil was enriched with 0.3% cotton seed meal (CSM) prior to plantation with tomato seedlings. After 30 days, the soil was homogenized in water and a sample was seeded on agar plates which served as a source for the isolation of EIP-N1 strain.

*Bacillus firmus* strain CNCM I-1582 showed highest sequence similarity (98.7%) to *Bacillus firmus*. *B. firmus* has been previously identified as a potential biological control agent against *Botrytis cinerea* (Yildiz, F., J. of Turkish Phytopathology (1991), 30, 11–22), and has also been identified as a new insect pathogen for a lepidoptera pest of *Ailanthus triphysa* (Varma, R. V., et al., J. of Invertebrate Pathology. (1986), 47, 379–380). However, there have not been any reports regarding nematicidal activity by this bacteria.

II. EIP-N2

*Bacillus cereus* strain CNCM I-1562 strain was isolated from a mixture of filtered sterile soil and 0.05% cotton seed meal (CSM) following a tube experiment in which tomato seedlings were planted. Ten days later the soil was homogenized in water and a sample was seeded on agar plates which served as a source for isolation of the *Bacillus cereus* strain CNCM I-1562 strain.

The *Bacillus cereus* strain CNCM I-1562 strain showed the highest sequence similarity to the following Bacilli species: *B.medusa* (99.3%); *B.cereus* (99.3%); *B.thuringiensis* (99.3%); and *B.mycoides* (99.3%). Further testing has indicated that *Bacillus cereus* strain CNCM I-1562 belongs to the *B. cereus* species.

III. Enzymatic Activity

The proteolytic and collagenolytic activities *Bacillus firmus* strain CNCM I-1582 and *Bacillus cereus* strain CNCM I-1562 (vegetative cells) as compared to other microorganisms were determined, and the results are shown in Tables I and II, respectively. It can be seen that the strains of the invention have significantly higher activity than the other microorganisms.

Without restricting the invention in any way, it is believed that proteolytic and collagenolytic activities play an important role in control of nematodes, either by direct effect on the cuticle of the nematode, or indirectly by increasing the release of ammonia which is known to be toxic to nematodes due to protein breakdown.

TABLE I

Proteolytic Activity

| Strain | Species | O.D./1.8 · 10$^9$CFU |
| --- | --- | --- |
| 20M | *Telluria mixta* | 0.238 |
| 555TT | Bacillus | 13.680 |
| CNCMI-1582 | *B. firmus* | 27.000 |
| CNCMI-1562 | *B. cereus* | 15.500 |
| 201 | Pseudomonas | 0.117 |
| 203 | Bacillus | 0.118 |
| 122 | Bacillus | 2.590 |

TABLE II

Collagenolytic Activity

| Bacteria | Species | O.D. | No. of cells/100 µl | Enzyme units |
| --- | --- | --- | --- | --- |
| CNCMI-1562 | *B. cereus* | 0.37 | 3 · 10$^6$ | 7.4 |
| C1 | *Pseudomonas putida* | 0.32 | 6 · 10$^7$ | 0.32 |
| #122 | Bacillus | 0.78 | 3.5 · 10$^5$ | 134 |
| #203 | Bacillus | 0.34 | 1.3 · 10$^7$ | 1.56 |
| #201 | Pseudomonas | 0.44 | 5 · 10$^6$ | 5.28 |
| 20M | *Telluria mixta* | 0.71 | 2 · 10$^6$ | 21.3 |
| C10 | *Pseudomonas cepasia* | 0.28 | 2.2 · 10$^7$ | 0.76 |
| B$_3$ | *B. cereus* | 0.84 | 6.2 · 10$^6$ | 8.12 |
| 555TT | Bacillus | 0.58 | 2 · 10$^5$ | 174 |
| CNCMI-1582 | *B. firmus* | 0.40 | 6.1 · 10$^5$ | 40 |

IV. Nematicidal Activity

*Bacillus firmus* strain CNCM I-1582 and *Bacillus cereus* strain CNCM I-1562 spores show a consistent and significant bionematicidal activity against root-knot nematodes under greenhouse as well as microplot conditions.

Figure 2:
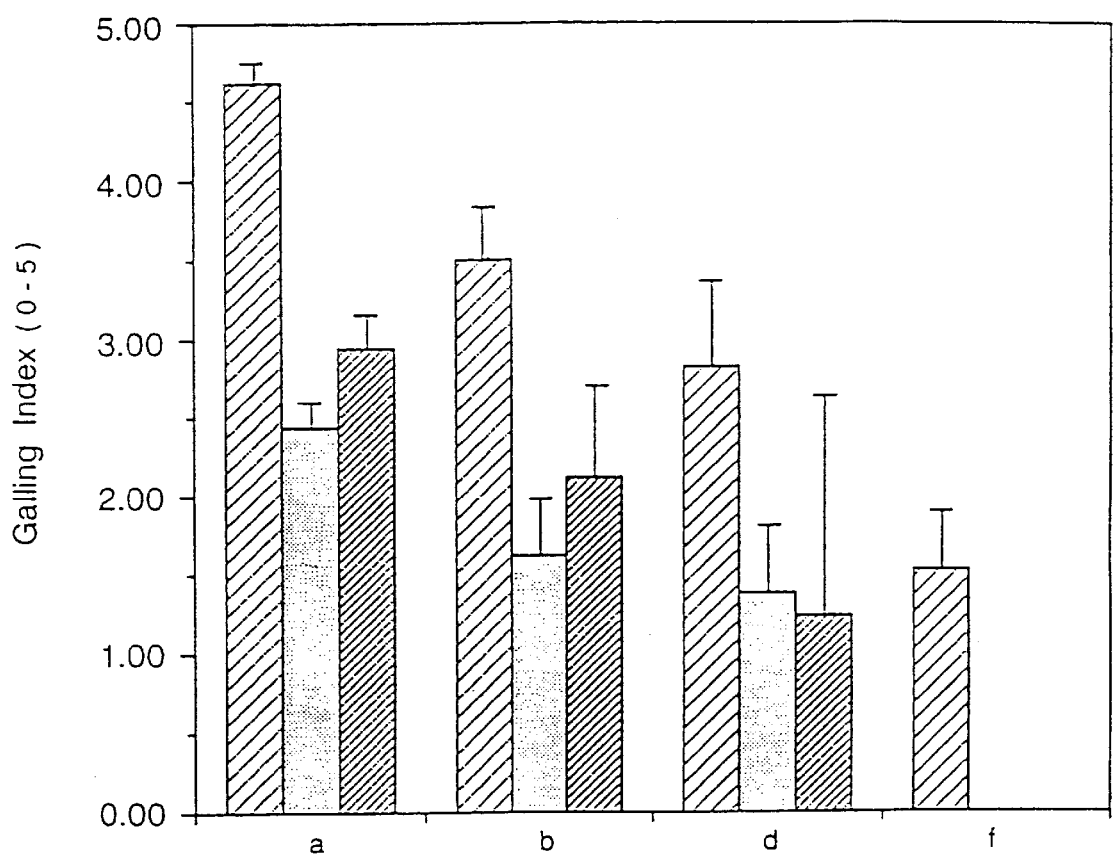
FIG. 2 shows results of a similar experiment to that shown in FIG. 1, obtained in microplots.

The results of a large number of experiments in which the nematicidal activity *Bacillus firmus* strain CNCM I-1582 and *Bacillus cereus* strain CNCM I-1562 against Meloidogyne spp. nematodes was determined under greenhouse conditions are summarized in FIG. 1 and the results in microplots are summarized in FIG. 2. The numbers in parenthesis in FIG. 1 indicate the number of trials averaged into the results, while the results in FIG. 2 are averages of 5 experiments. The diseased plants were treated with no bacterial spores (☐), *Bacillus firmus* strain CNCM I-1582 (▨) or *Bacillus cereus* strain CNCM I-1562 (▨). The following supplements were used in the experiments: a) none; b) gelatin; c) gelatin hydrolysate; d) gelatin+cotton seed meal; e) casein hydrolysate; and f) Nemacur®.

When bacterial spores alone (no supplement added) were applied to the plants, there was a 40–50% reduction in root-knot nematode infestation as compared to the control in which no bacteria was added, both in greenhouse and microplot trials. When supplements such as gelatin (0.2% w/w) or a mixture of gelatin and cotton seed meal (CSM) at concentrations of 0.05% and 0.25%, respectively, were applied to the plants without bacteria, there was a reduction of 30–40% in the galling index. However, when both bacteria and supplement(s) were added together, there was an additive, intensified effect resulting in a decrease of 9–100% and 70% in the galling index in greenhouse and microplot trials, respectively. Similar results were obtained with hydrolysates of gelatin and casein.

Other supplements, either alone or in combination can be used to increase the nematicidal activity of the bacteria. These include vegetative grains such as pea, bean and humus flours, and extracts from animal sources such as feather powder, powdered meat and other inexpensive protein hydrolysates. Examples of preferred supplement combinations are crude gelatinous material and CSM, or whey protein and CSM, at concentrations of 0.1% and 0.25%, respectively.

Spores formulated in peat moss or silica prior to mixing with pot soil in the presence or absence of supplement showed the same nematicidal activity as compared to the regular application technique described above.

In general, the bacteria and the supplements had a positive effect on the top fresh weight of the tomato plant. When used separately, they increased the top fresh weight by 50–100% as compared to control. However, when used in combination, the bacteria and supplement gave an increase of 200–300%.

V. Stability The *Bacillus firmus* strain CNCM I-1582 and *Bacillus cereus* strain CNCM I-1562 strains showed superior long-term stability with respect to nematicidal activity over numerous other strains, some of which appear in Tables I and II. For example, the 555TT strain which showed high collagenolytic activity had poor stability at RT or 4° C.

In summary, the *Bacillus firmus* strain CNCM I-1582 and *Bacillus cereus* strain CNCM I-1562 strains were chosen due to their superior performance in the three categories of nematicidal activity, enzyme activity and stability.

VI. Nematicidal Compositions

A typical nematicidal composition will include the active ingredient *Bacillus firmus* strain CNCM I-1582 or *Bacillus cereus* strain CNCM I-1562 spores), an appropriate supplement, a carrier which is compatible to the activity of the spores as well as to the plant being treated, and, preferably, a surfactant. Examples of supplements which may be added are 0.1% Scanpro™ 210/F (crude gelatinous material)+0.25% CSM, or 0.1% AMP™ 800 (whey protein)+0.25% CSM.

The composition can be modified in accordance with the application technique by which it will be used: 1) application through the irrigation system; 2) mixing in the soil of the plants; 3) seed coating.

The bacterial strain EIPN-1 identified herein as CNCM I-1556 has been replaced by CNCM I-1582, which is equivalent.

What is claimed is:

1. A biologically pure strain selected from the group consisting of *Bacillus firmus* CNCM I-1582 having nematicidal activity and a biologically pure nematicidally active mutant of said strain having all of the identifying characteristics thereof.

2. A biologically pure nematicidally active strain according to claim 1 wherein said strain is said mutant.

3. A nematicidal composition for use in plant protection comprising, as an active ingredient, an effective amount of bacteria or spores of a biologically pure strain selected from the group consisting of *Bacillus firmus* CNCM I-1582, and a biologically pure nematicidally active mutant of said strain having all of the identifying characteristics therefore, said composition further containing a carrier.

4. A composition according to claim 3 further comprising a supplement selected from the group consisting of gelatin, gelatin hydrolysate, crude gelatinous material, whey protein, casein hydrolysate and cotton seed meal, wherein said supplement improves the nematicidal activity of the bacteria.

5. A method for controlling plant-pathogenic nematodes, comprising applying to a plant a composition according to claim 3 or 4.

6. A method for controlling plant-pathogenic nematodes, comprising applying to said plant a nematicidally effective amount of bacteria or spores of a biologically pure strain selected from the group consisting of *Bacillus firmus* CNCM I-1582, and a biologically pure nematicidally active mutant of said strain having all of the identifying characteristics thereof.

7. A method according to claim 6 or 5, wherein the nematodes are root-knot disease causing nematodes.

8. A method according to claim 6 or 5, wherein the nematodes belong to the species Meloidogyne.

9. A nematicidal composition for use in plant protection comprising, as an active ingredient, an effective amount of bacteria or spores of a biologically pure strain selected from the group consisting of *Bacillus cereus* CNCM I-1562, and a biologically pure nematicidally active mutant of said strain having all of the identifying characteristics thereof, said composition further containing a carrier.

10. A composition according to claim 9 further comprising a supplement selected from the group consisting of gelatin, gelatin hydrolysate, crude gelatinous material, whey protein, casein hydrolysate and cotton seed meal, wherein said supplement improves the nematicidal activity of the bacteria.

11. A method for controlling plant-pathogenic nematodes comprising applying to said plant a composition according to claim 9 or 10.

12. A method for controlling plant-pathogenic nematodes, comprising applying to said plant a nematicidally effective amount of bacteria or spores of a biologically pure strain selected from the group consisting of *Bacillus cereus* strain CNCM I-1562 and a nematicidally active biologically pure mutant of said strain having all of the identifying characteristics thereof.

13. A method according to claim 12 or 11, wherein the nematodes are root-knot disease causing nematodes.

14. A method according to claim 12 or 11 wherein the nematodes belong to the species Meloidogyne.

* * * * *